United States Patent
Couture

(10) Patent No.: US 9,861,429 B2
(45) Date of Patent: Jan. 9, 2018

(54) MECHANICAL CUTTING SYSTEM FOR SURGICAL FORCEPS

(71) Applicant: COVIDIEN LP, Mansfield, MA (US)

(72) Inventor: Gary M. Couture, Ward, CO (US)

(73) Assignee: COVIDIEN LP, Mansfield, MA (US)

( * ) Notice: Subject to any disclaimer, the term of this patent is extended or adjusted under 35 U.S.C. 154(b) by 461 days.

(21) Appl. No.: 14/670,037

(22) Filed: Mar. 26, 2015

(65) Prior Publication Data

US 2016/0278849 A1    Sep. 29, 2016

(51) Int. Cl.
*A61B 18/14* (2006.01)
*A61B 17/29* (2006.01)
*A61B 90/00* (2016.01)

(52) U.S. Cl.
CPC .......... *A61B 18/1445* (2013.01); *A61B 90/03* (2016.02); *A61B 2017/2927* (2013.01); *A61B 2017/2936* (2013.01); *A61B 2018/1455* (2013.01); *A61B 2090/037* (2016.02)

(58) Field of Classification Search
CPC ............ A61B 18/1442; A61B 18/1445; A61B 18/1447; A61B 18/085; A61B 2018/1452; A61B 2018/1455; A61B 2018/0063; A61B 2018/00607; A61B 17/295; A61B 2017/2927; A61B 2017/2929; A61B 2017/2936; A61B 90/03
USPC ............................... 606/41, 50–52, 205, 207
See application file for complete search history.

(56) References Cited

U.S. PATENT DOCUMENTS

| | | | |
|---|---|---|---|
| 2,068,721 A | 1/1937 | Wappler | |
| 4,655,216 A | 4/1987 | Tischer | |
| 6,174,309 B1 | 1/2001 | Wrublewski et al. | |
| 6,425,896 B1 | 7/2002 | Baltschun et al. | |
| 7,041,102 B2 | 5/2006 | Truckai et al. | |
| 7,744,615 B2 | 6/2010 | Couture | |
| 7,955,332 B2 | 6/2011 | Arts et al. | |
| 8,241,282 B2 | 8/2012 | Unger et al. | |
| 8,425,511 B2 | 4/2013 | Olson | |
| 8,591,510 B2 | 11/2013 | Allen, IV et al. | |
| 8,628,557 B2 | 1/2014 | Collings et al. | |
| 8,647,343 B2 | 2/2014 | Chojin et al. | |
| 2004/0199181 A1 | 10/2004 | Knodel et al. | |
| 2007/0078459 A1 | 4/2007 | Johnson et al. | |
| 2008/0015567 A1 | 1/2008 | Kimura | |
| 2011/0054467 A1 | 3/2011 | Mueller et al. | |
| 2011/0319886 A1* | 12/2011 | Chojin ............... A61B 18/1445 606/37 |

(Continued)

*Primary Examiner* — Thomas Giuliani

(57) ABSTRACT

A surgical instrument includes a housing having an elongated shaft that extends therefrom and a handle pivotable relative thereto. An end effector assembly is attached to a distal end of the shaft and includes first and second jaw members. The first jaw member is pivotably attached to a distal end of the shaft and the second jaw member extends along a longitudinal axis defined therethrough and fixed to the distal end of the shaft by a living hinge. The first jaw member, upon actuation of the handle, is movable relative to the second jaw member between spaced-apart position, an approximated position for grasping tissue, and a second position for over-compressing tissue grasped between jaw members. A knife is disposed within a channel defined within the second jaw member and is exposed to cut tissue when the first jaw member over-travels to over-compress the second jaw member.

14 Claims, 6 Drawing Sheets

(56) References Cited

U.S. PATENT DOCUMENTS

2012/0041438 A1    2/2012   Nau, Jr. et al.
2012/0296332 A1   11/2012   Chernov et al.
2013/0018372 A1    1/2013   Sims et al.
2013/0103031 A1    4/2013   Garrison
2013/0325004 A1   12/2013   Greep
2014/0046323 A1    2/2014   Payne et al.

* cited by examiner

MECHANICAL CUTTING SYSTEM FOR SURGICAL FORCEPS

BACKGROUND

Technical Field

The present disclosure relates to surgical instruments and, more particularly, to surgical forceps having mechanical cutting capabilities.

Background of Related Art

Many surgical instruments include one or more movable handles, levers, actuators, triggers, etc. for actuating and/or manipulating one or more functional components of the surgical instrument. For example, a surgical forceps may include a movable handle that is selectively compressible relative to a stationary handle for moving first and second jaw members of the forceps between spaced-apart and approximated positions for grasping tissue therebetween. Such a forceps may further include additional components such as a trigger for selectively deploying a knife between the jaw members to cut tissue grasped therebetween.

As can be appreciated, as additional functional components are added to the surgical instrument, additional deployment structures or deployment structures capable of actuating more than one component are required. However, multiple deployment structures and/or combined deployment structures may be limited by spatial constraints within the housing of the surgical instrument and/or functional constraints of the components.

SUMMARY

As a result there exists a need to provide a simple yet effective cutting mechanism for surgical instruments that alleviates the need for additional spatial considerations in the housing. As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

The present disclosure relates to a surgical instrument having a housing with an elongated shaft that extends therefrom and a handle pivotably coupled to the housing and moveable relative thereto. The surgical instrument also includes an end effector assembly having first and second jaw members, the first jaw member pivotably attached to a distal end of the shaft and the second jaw member extending along a longitudinal axis defined therethrough and fixed to the distal end of the shaft by a living hinge. The first jaw member, upon actuation of the handle relative to the housing, is movable relative to the second jaw member between a spaced-apart position, an approximated position for grasping tissue between the first and second jaw members, and a second position for providing an over-compressive force to the jaw members. A knife is disposed within a channel defined within the second jaw member.

When the handle is initially actuated relative to the housing, the first jaw member is moved from the spaced-apart position to the approximated position to grasp tissue between jaw members. When the handle is further actuated from the approximated position to the second position, the first jaw member over-travels past the longitudinal axis to over-compress the jaw members and the second jaw member deflects relative to the longitudinal axis against the bias of the living hinge thereby exposing the knife from the channel to cut tissue grasped between jaw members.

In one embodiment according to the present disclosure, the surgical instrument includes a drive rod that extends through the shaft having a drive pin at a distal end thereof. Actuation of the drive rod moves the first jaw member relative to the second jaw member. The first jaw member includes a flange that extends proximally therefrom having an aperture defined therein for receiving a pivot pin. The first jaw member is rotatable about the pivot pin upon actuation of the drive rod. The flange includes a cam slot defined therein configured to receive the drive pin to move the first jaw member relative to the second jaw member.

In one embodiment according to the present disclosure, in the approximated position, the jaw members grasp tissue with a clamping pressure in the range of about 3 kg/cm$^2$ to about 16 kg/cm$^2$. In yet another embodiment, when the clamping pressure between jaw members exceeds 16 kg/cm$^2$, the second jaw member deflects relative to the longitudinal axis to expose the knife.

In still another embodiment according to the present disclosure, the first jaw member includes a channel defined therein in vertical registration with the channel defined within the second jaw member. The channel defined in the first jaw member is configured to receive the knife as the first jaw member over-travels past the longitudinal axis and the second jaw member deflects about the living hinge. In yet another embodiment, the over-travel of the first jaw member against the second jaw member causes the second jaw member to deflect in a tip-biased manner thereby initially exposing a distal end of the knife and cutting tissue in a distal-to-proximal manner as the knife is further exposed.

The present disclosure also relates to a surgical instrument having an end effector assembly including first and second jaw members. The first jaw member is pivotable relative to the second jaw member and the second jaw member extends along a longitudinal axis defined therethrough. The second jaw member includes a living hinge at a proximal end thereof. The first jaw member is movable relative to the second jaw member between a spaced-apart position, an approximated position for grasping tissue between the first and second jaw members, and a second position for providing an over-compressive force to the jaw members. A knife is disposed within a channel defined within the second jaw member.

When the first jaw member is moved from the spaced-apart position to the approximated position to grasp tissue between jaw members, and further moved from the approximated position to the second position to over-compress the jaw members, the first jaw member over-travels past the longitudinal axis and the second jaw member deflects relative to the longitudinal axis against the bias of the living hinge thereby exposing the knife from the channel to cut tissue grasped between jaw members.

In one embodiment, the jaw members grasp tissue with a clamping pressure in the range of about 3 kg/cm$^2$ to about 16 kg/cm$^2$. In yet another embodiment, when the clamping pressure between jaw members exceeds 16 kg/cm$^2$, the second jaw member deflects relative to the longitudinal axis to expose the knife.

In yet another embodiment, the first jaw member includes a channel defined therein in vertical registration with the channel defined within the second jaw member. The channel defined in the first jaw member is configured to receive the knife as the first jaw member over-travels past the longitudinal axis and the second jaw member deflects about the living hinge.

In still another embodiment, the over-travel of the first jaw member against the second jaw member causes the second jaw member to deflect in a tip-biased manner thereby initially exposing a distal end of the knife and cutting tissue in a distal-to-proximal manner as the knife is further exposed.

The present disclosure also relates to a method for treating and cutting tissue, actuating a handle of a surgical instrument to grasp tissue between a pair of first and second jaw members of an end effector assembly under a first pressure. The method also includes applying electrosurgical energy to the jaw members to treat tissue grasped between the end effectors and further actuating the handle to cause the first jaw member to over-travel past a longitudinal axis defined through the second jaw member and over-compress the jaw members thus causing the second jaw member to deflect about a living hinge relative to the longitudinal axis and expose a knife for severing tissue grasped between the jaw members.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
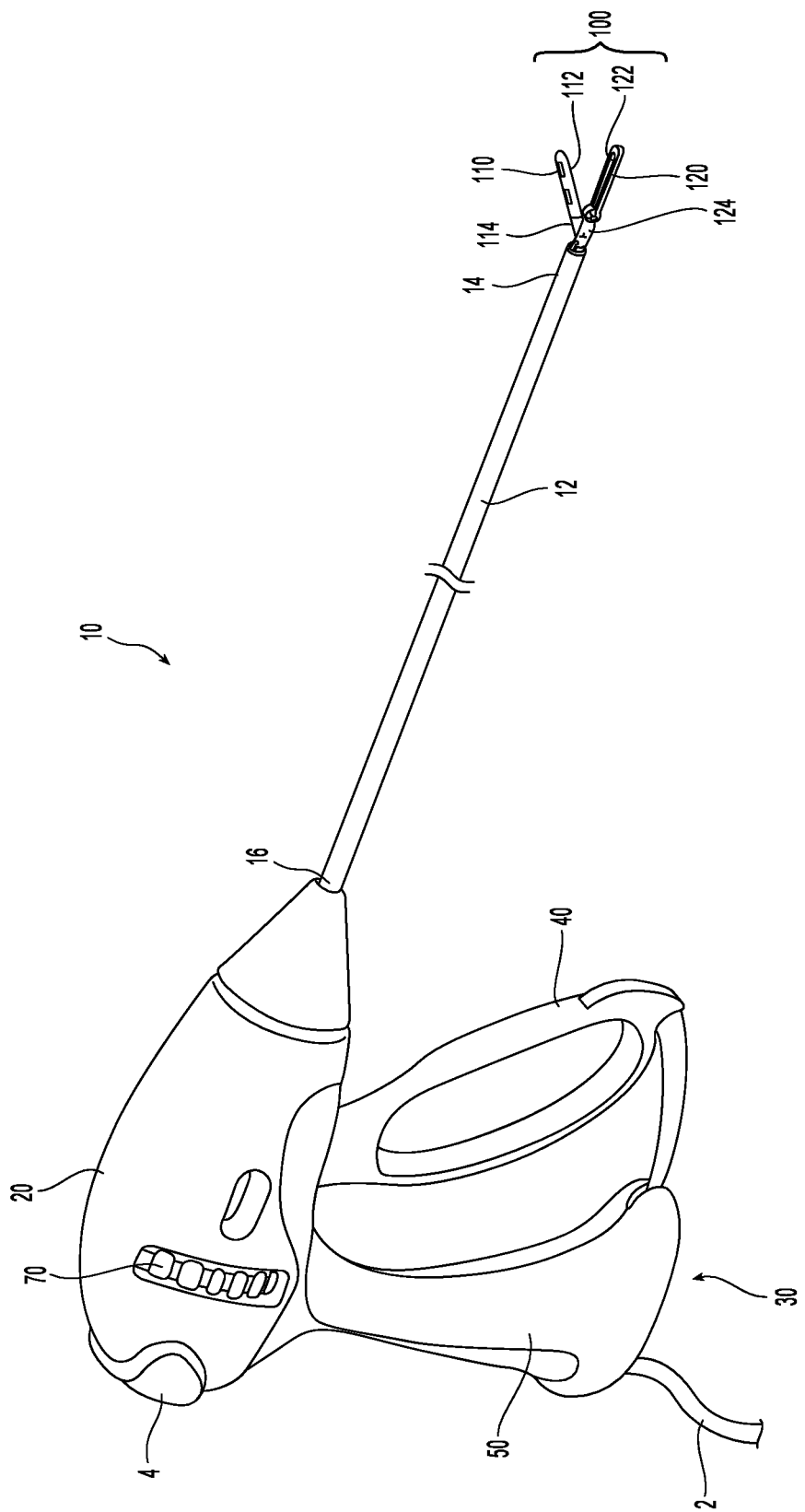
FIG. 1 is a front, perspective view of an endoscopic surgical forceps configured for use in accordance with the present disclosure.

Referring generally to FIG. 1, a forceps provided in accordance with the present disclosure is shown generally identified by reference numeral 10. Forceps 10, as will be described below, may be configured to operate in both a bipolar mode, e.g., for grasping, treating, and/or dissecting tissue, and a monopolar mode, e.g., for treating and/or dissecting tissue. Although the present disclosure is shown and described with respect to forceps 10, the aspects and features of the present disclosure are equally applicable for use with any suitable surgical instrument or portion(s) thereof for selectively actuating, moving, and/or deploying the assemblies and/or components of the surgical instrument. Obviously, different connections and considerations apply to each particular instrument and the assemblies and/or components thereof; however, the aspects and features of the present disclosure remain generally consistent regardless of the particular instrument, assemblies, and/or components provided.

Continuing with reference to FIG. 1, forceps 10 includes a housing 20, a handle assembly 30, a rotating assembly 70, and an end effector assembly 100 including first and second jaw members 110 and 120, respectively. Forceps 10 further includes a shaft 12 having a distal end 14 configured to mechanically engage end effector assembly 100 and a proximal end 16 that mechanically engages housing 20. Forceps 10 also includes an electrosurgical cable 2 that connects forceps 10 to a generator (not shown) or other suitable power source, although forceps 10 may alternatively be configured as a battery powered instrument. Cable 2 includes wires (not shown) extending therethrough that have sufficient length to extend through shaft 12 in order to provide electrical energy to at least one electrically-conductive surface 112, 122 (FIG. 2A) of jaw members 110, 120, respectively, of end effector assembly 100, e.g., upon activation of a switch 4. Other suitable ways of delivering energy to the electrically-conductive surfaces 112, 122 are contemplated including other suitable power sources, e.g., forceps 10 may alternatively be configured as a battery-powered forceps 10. Rotating assembly 70 is rotatable in either direction to rotate end effector assembly 100 relative to housing 20. Housing 20 houses the internal working components of forceps 10, which are described in detail below.

Referring to FIGS. 2A-2D, end effector assembly 100 is attached at a distal end 14 of shaft 12 and includes opposing jaw members 110, 120 pivotably coupled to one another. Each of the jaw members 110 and 120 includes a jaw body 111, 121 supporting the respective electrically-conductive surface 112, 122, and a respective proximally-extending jaw flange 114, 124. Flanges 114, 124 are pivotably coupled to one another about a pivot 75 to permit movement of jaw members 110, 120 relative to one another between a spaced-apart position (FIG. 2A), an approximated position (FIG. 2B) for grasping tissue between surfaces 112, 122 and an over-compressed position (FIG. 2C) for deploying a knife 184. More details with respect to the actuation of the jaw members 110 and 120 are explained below.

One or both of surfaces 112, 122 are adapted to connect to a source of energy (not explicitly shown), e.g., via the wires (not shown) of cable 2 (FIG. 1) and are configured to conduct energy through tissue grasped therebetween to treat, e.g., seal, tissue. More specifically, end effector assembly 100 defines a bipolar configuration wherein surface 112 is charged to a first electrical potential and surface 122 is charged to a second, different electrical potential such that an electrical potential gradient is created for conducting energy between surfaces 112, 122 and through tissue grasped therebetween for treating e.g., sealing, tissue. Activation switch 4 (FIG. 1) is operably coupled between the source of energy (not shown) and surfaces 112, 122, thus allowing the user to selectively apply energy to surfaces 112, 122 of jaw members 110, 120, respectively, of end effector assembly 100 when activated.

End effector assembly 100 is designed as a unilateral assembly, i.e., where jaw member 120 is relatively fixed relative to shaft 12 and jaw member 110 is movable relative to shaft 12 and fixed jaw member 120. Jaw member 120 is attached to a distal end of jaw flange 124 by a living hinge 127 which is configured to allow the jaw member 120 to deflect relative to a longitudinal axis "A" defined along jaw member 120 when enough pressure is exerted on jaw member 120 by jaw member 110 (See FIG. 2C). A knife channel 129 is defined within jaw member 120 to house the knife 184 therein and permit deployment of the knife 184 therefrom as explained in more detail below.

With reference again to FIG. 1, handle assembly 30 includes a movable handle 40 and a fixed handle 50. Fixed handle 50 is integrally associated with housing 20 and movable handle 40 is movable relative to fixed handle 50. Movable handle 40 is movable relative to fixed handle 50 between an initial position, wherein movable handle 40 is spaced from fixed handle 50, a first compressed position, wherein movable handle 40 is compressed towards fixed handle 50, and a second compressed position wherein moveable handle 40 is further compressed relative to handle 50. A biasing member (not shown) may be provided to bias movable handle 40 towards the initial position. Movable handle 40 is ultimately connected to a drive assembly (not explicitly shown) which ultimately imparts movement of a drive rod 85 which, in turn, moves the jaw members 110, 120 between the spaced-apart position (FIG. 2A), corresponding to the initial position of movable handle 40, and the approximated position (FIG. 2B), corresponding to an initial compressed position of movable handle 40, and an over-compressed position (FIG. 2C) corresponding to a second compressed position of handle 40. Any suitable drive assembly for this purpose may be provided.

Figure 2A:
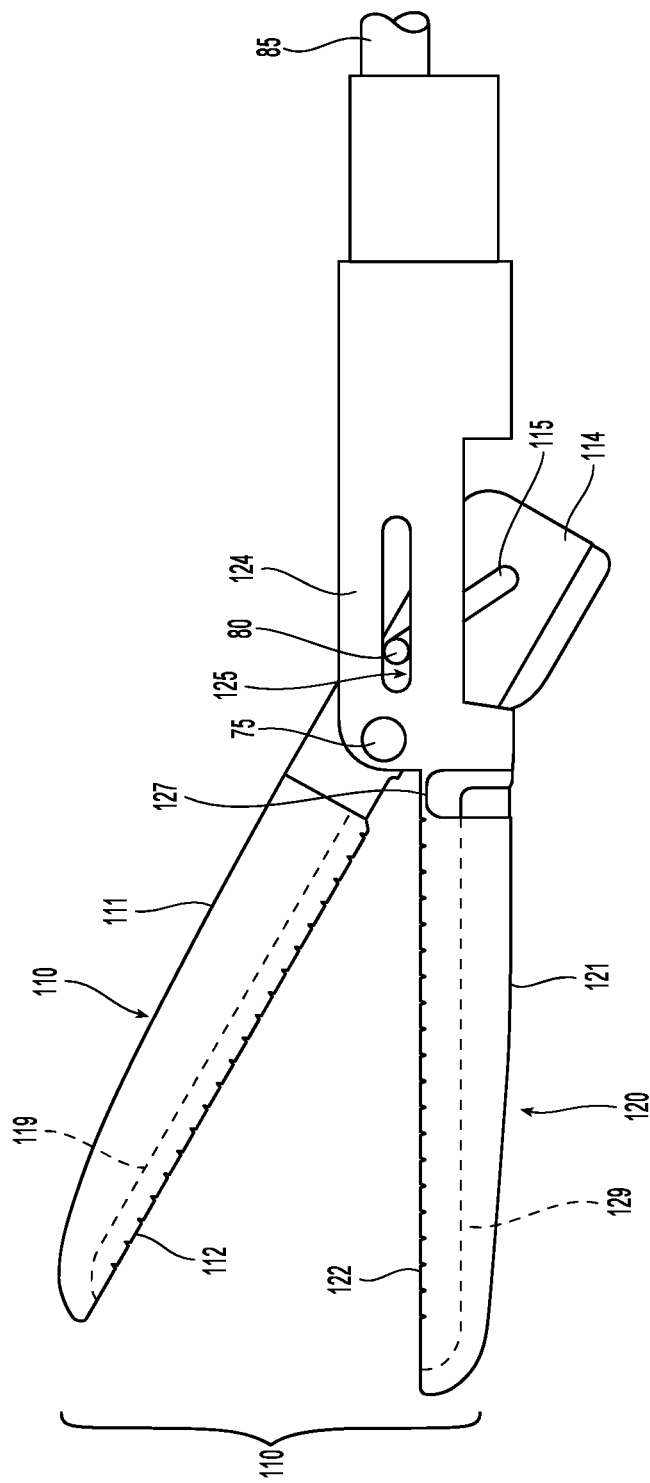
FIG. 2A is a side view of an end effector assembly of the surgical forceps according to the present disclosure having first and second jaw members shown in a spaced-apart position.
Figure 2B:
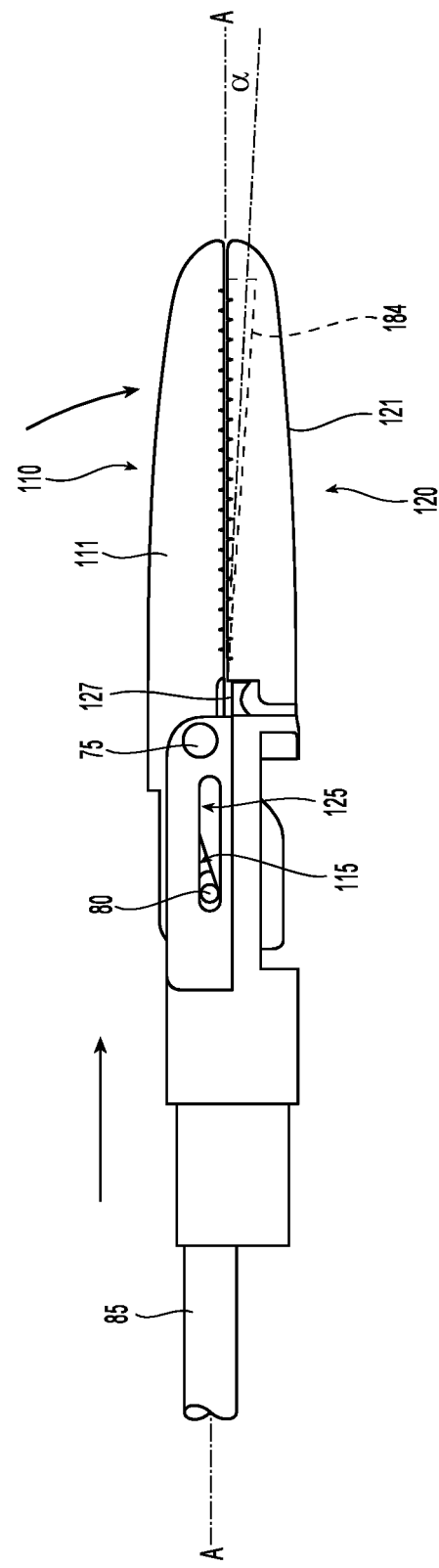
FIG. 2B is a side view of the end effector assembly of FIG. 2A with the first and second jaw members shown in an approximated position.
Figure 2C:
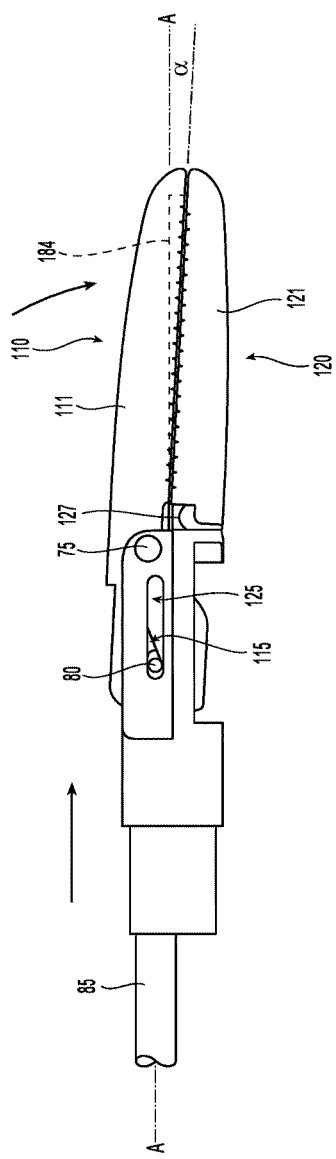
FIG. 2C is a side view of the end effector assembly of FIG. 2A with the first and second jaw members shown in an over-compressed position.

As best shown in FIGS. 2A-2C, the corresponding flanges 114 and 124 of respective jaw members 110 and 120 each include a cam slot 115 and 125 defined therein configured to commonly receive a drive pin 80 attached to a distal end of the drive rod 85. Movement of the handle 40 from the initial position to the initial compressed position and potentially the second compressed position, in turn, translates the drive bar 85 and the drive pin 80 to correspondingly actuate the jaw members 110 and 120. More particularly, upon actuation of handle 40, the drive pin 80 is pulled proximally within the corresponding cam slots 115 and 125 to cam the jaw member 110 towards the approximated position (FIG. 2B) with jaw member 120 which enables a user to grasp and treat tissue. In this position, the jaw members 110 and 120 are parallel to the longitudinal axis "A" defined through jaw member 120. For example, when sealing tissue, the jaw members 110 and 120 when approximated may be configured to provide an initial clamping pressure on tissue within the range of about 3 kg/cm$^2$ to about 16 kg/cm$^2$. A specific gap distance between jaw members may facilitate and enhance the sealing process, e.g., a gap within the range of about 0.001 inches to about 0.006 inches.

As best shown in FIG. 2C, when the handle 40 is moved to the second compressed position, the drive pin 80 applies an over-compressive force to the jaw members 110 and 120 which provides greater pressure between jaw members 110 and 120 and causes jaw member 110 to over-travel and jaw member 120 to deflect about the living hinge 127 to an angle α relative to the longitudinal axis "A". As used herein, the term over-travel is defined to mean that the jaw member 110 travels past parallel with jaw member 120 due to the over-compressive force applied by handle 40. As used herein, the term over-compress is used to define a force beyond the normal compressive forces against tissue associated with tissue sealing (in the range of about 3 kg/cm$^2$ to about 16 kg/cm$^2$). In the embodiments described herein, the over-compressive force applied by handle 40 is offset or concentrated to jaw member 110 to cause jaw member 110 to over-travel past parallel and cause jaw member 120 to deflect.

In one embodiment, the clamping pressure exceeds 16 kg/cm$^2$ to start initial deflection of the second jaw member 120 about the living hinge 127 with respect to the longitudinal axis "A". While in both the approximated position or the over-compressed position with jaw member 120 deflected to exposed knife 184, a series of stop members (not explicitly shown) disposed along the sealing surfaces 112, 122 of one or both jaw members, 110, 120 respectively, are configured to maintain a gap distance between jaw members 110 and 120 in the range of about 0.001 inches to about 0.006 inches. As a result, the over-compressive force of the handle 40 in the second position is concentrated to deflect jaw member 120 and expose knife 184 and does not necessarily affect the compressive force against the tissue grasped between jaw members 110 and 120.

When the jaw member 120 deflects about the living hinge 127, knife 184 is exposed and acts to sever tissue disposed between the jaw members 110 and 120. More particularly, knife 184 is coupled to flange 124 and extends therefrom into a channel 129 defined within jaw member 120. As the drive pin 80 is pulled proximally past the approximated position and jaw member 110 exerts an over-compressive force against jaw member 120, jaw member 120 deflects against the bias of the living hinge 127 at an angle α relative to the longitudinal axis "A".

As jaw member 120 deflects, both jaw members 110 and 120 are forced past parallel with longitudinal axis "A". Moreover, as jaw member 120 deflects, knife 184 is exposed and projects from channel 129 through tissue disposed between the jaw members 110 and 120 and into a corresponding channel 119 defined in jaw member 110 in vertical registration with channel 129. When handle 40 is released, the drive pin 80 retracts distally to an at-rest position forcing the jaw members 110 and 120 to the spaced-apart position. As a result thereof, the over-compressive force against jaw member 120 is released and jaw member 120 returns to a position parallel with longitudinal axis "A" under the return bias of living hinge 127. The severed and treated tissue may then be removed from between jaw members 110 and 120.

Figure 2D:
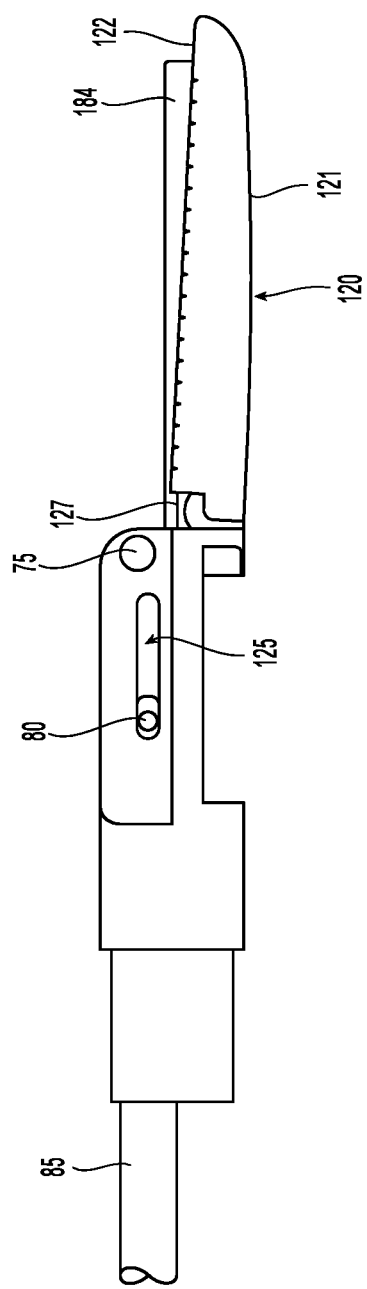
FIG. 2D is a side view of the second or fixed jaw member of the end effector assembly of FIG. 2A showing exposure of a knife upon deflection of the second or fixed jaw member.
Figure 3:
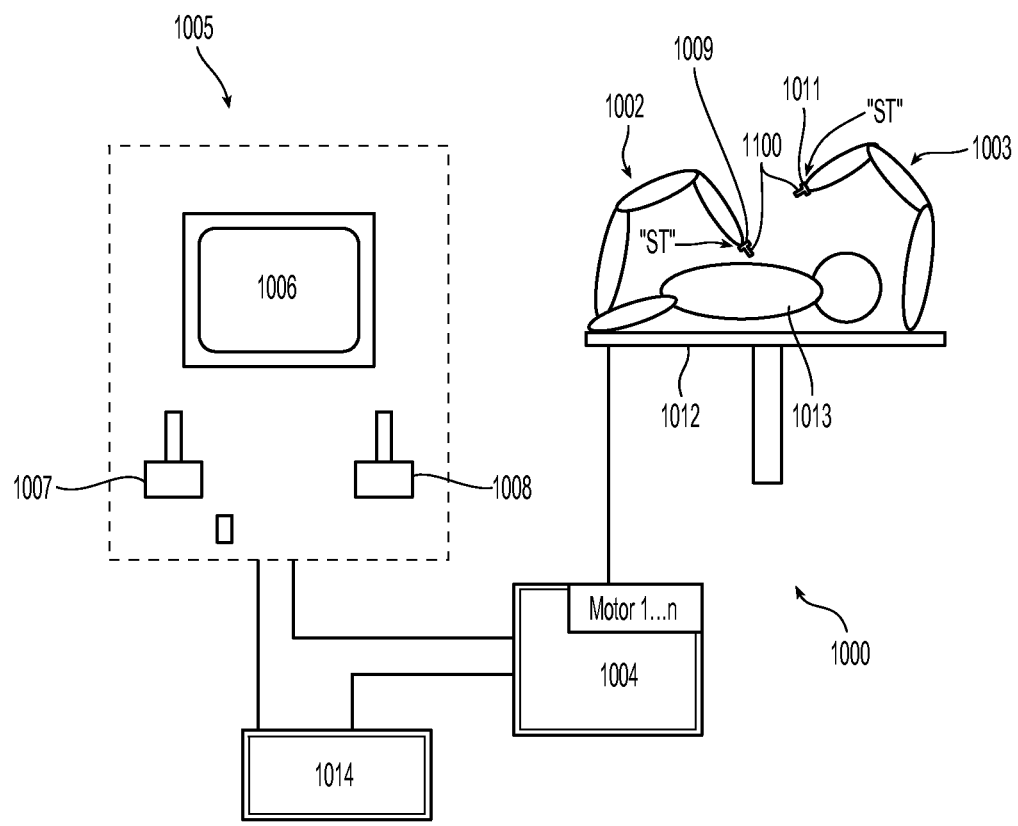
FIG. 3 is a schematic illustration of a robotic system configured for use in accordance with the present disclosure.

Referring to FIGS. 1-2D, the use and operation of forceps 10 for grasping, treating and/or cutting tissue, is described. FIGS. 1 and 2A show jaw members 110, 120 disposed in the spaced-apart position such that end effector assembly 100 may be maneuvered into position so tissue may be grasped, treated, e.g., sealed, and/or cut. Movable handle 40 is compressed, or pulled proximally relative to fixed handle 50 such that jaw member 110 is pivoted relative to jaw member 120 from the spaced-apart position to the approximated position to grasp tissue therebetween, as shown in FIG. 2B. In this approximated position, energy may be supplied, e.g., via activation of switch 4, to plate 112 of jaw member 110 and/or plate 122 of jaw member 120 and conducted through tissue to treat tissue, e.g., to effect a tissue seal or otherwise treat tissue in the bipolar mode of operation. In this instance the jaw members 110 and 120 may be reopened by releasing handle 40 to release the tissue.

Alternatively, the handle 40 may be further compressed to the second position to apply an over-compressive force to the jaw members 110 and 120 to over-travel jaw member 110 against jaw member 120 past longitudinal axis "A" thereby deflecting jaw member 120 relative to longitudinal axis "A" and exposing knife 184 to sever the tissue disposed between jaw members 110 and 120. Jaw members 110 and 120 may be reopened by releasing handle 40 to release the tissue.

In one embodiment, the over-travel of jaw member 110 against jaw member 120 causes jaw member 120 to deflect in a tip-biased manner, thereby exposing a distal end of the knife 184 initially and cutting tissue in a distal-to-proximal manner.

Alternatively, movable handle 40 may be compressed, or pulled proximally relative to fixed handle 50 such that jaw member 110 is pivoted relative to jaw member 120 from the spaced-apart position to the approximated position and further compressed to the second position to over-compress jaw member 110 against jaw member 120, as shown in FIG. 2C. In this over-compressed position, the knife 184 is exposed and will sever the tissue disposed between jaw members 110 and 120. As can be appreciated, this allows the surgeon to utilize the forceps 10 in a conventional cutting manner without energizing or treating tissue.

In yet another embodiment, movable handle 40 may be compressed relative to fixed handle 50 such that jaw member 110 is pivoted relative to jaw member 120 from the spaced-apart position to the approximated position and further compressed to the second position to over-compress jaw member 110 against jaw member 120, as shown in FIG. 2C. In this over-compressed position, simultaneous (or substantially simultaneously) the knife 184 is exposed to cut tissue between jaw members 110 and 120 while energy is being supplied via activation of switch 4 to the tissue. As can be appreciated this allows the user to grasp, cut and treat tissue at relatively the same time or at least substantially simultaneously cut and treat tissue at the same time.

One or more safety features may be employed to prevent exposure of the knife 184 prior to activation of energy. For example, switch 4 may be electrically connected to a mechanical stop (not shown) that prevents the exposure of the knife 184 prior to activating energy. One embodiment may include the activation switch 4 being disposed in the pathway of the movable handle 40 such that switch 4 must be deployed to move handle 40 past the approximated position. In another embodiment, a mechanical release (not shown) is employed with activation switch 4 that releases handle 40 to permit movement past the approximated position.

When tissue cutting is complete, handle 40 may be released to allow jaw members 110 and 120 to initially return to a parallel configuration along longitudinal axis "A" thereby allowing knife 184 to retract back into channel 129. Further release of handle 40 moves jaw members 110, 120 back to the spaced-apart position (FIG. 2A) to release the treated and/or divided tissue.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Referring to FIG. 4, a medical work station is shown generally as work station 1000 and may generally include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of the embodiments disclosed hereinabove.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a housing having an elongated shaft that extends therefrom;
   a handle pivotably coupled to the housing and moveable relative thereto;
   an end effector assembly including first and second jaw members, the first jaw member pivotably attached to a distal end of the shaft and the second jaw member extending along a longitudinal axis defined therethrough and fixed to the distal end of the shaft by a living hinge, the first jaw member, upon actuation of the handle relative to the housing, is movable relative to the second jaw member between a spaced-apart position, an approximated position for grasping tissue between the first and second jaw members, and a second position for providing an over-compressive force to the jaw members; and
   a knife disposed within a channel defined within the second jaw member,
   wherein, when the handle is initially actuated relative to the housing, the first jaw member is moved from the spaced-apart position to the approximated position to grasp tissue between the first and second jaw members, and when the handle is further actuated from the approximated position to the second position, the first jaw member over-travels past the longitudinal axis to provide an over-compressive force to the jaw members such that the second jaw member deflects relative to the longitudinal axis against a bias of the living hinge exposing the knife from the channel to cut tissue grasped between the first and second jaw members.

2. The surgical instrument according to claim 1, further comprising a drive rod extending through the shaft, the drive rod including a drive pin at a distal end thereof, wherein actuation of the drive rod moves the first jaw member relative to the second jaw member.

3. The surgical instrument according to claim 2, wherein the first jaw member includes a flange that extends proximally therefrom, the flange including an aperture defined therein for receiving a pivot pin, the first jaw member rotatable about the pivot pin upon actuation of the drive rod.

4. The surgical instrument according to claim 3, wherein the flange includes a cam slot defined therein, the drive pin moveable within the cam slot to move the first jaw member relative to the second jaw member.

5. The surgical instrument according to claim 1, wherein, in the approximated position, the jaw members are configured to grasp tissue with a clamping pressure in the range of about 3 kg/cm$^2$ to about 16 kg/cm$^2$.

6. The surgical instrument according to claim 5, wherein when the clamping pressure between jaw members exceeds 16 kg/cm$^2$, the second jaw member deflects relative to the longitudinal axis to expose the knife.

7. The surgical instrument according to claim 1, wherein the first jaw member includes a channel defined therein in vertical registration with the channel defined within the second jaw member, the channel defined in the first jaw member configured to receive the knife as the first jaw member over-travels past the longitudinal axis and the second jaw member deflects about the living hinge.

8. The surgical instrument according to claim 1, wherein the over-travel of the first jaw member against the second jaw member causes the second jaw member to deflect in a tip-biased manner thereby initially exposing a distal end of the knife and cutting tissue in a distal-to-proximal manner as the knife is further exposed.

9. A surgical instrument, comprising:
   an end effector assembly including first and second jaw members, the first jaw member pivotable relative to the second jaw member, the second jaw member extending along a longitudinal axis defined therethrough and including a living hinge at a proximal end thereof, the first jaw member movable relative to the second jaw member between a spaced-apart position, an approximated position for grasping tissue between the first and second jaw members, and a second position for providing an over-compressive force to the jaw members; and
   a knife disposed within a channel defined within the second jaw member,
   wherein when the first jaw member is moved from the spaced-apart position to the approximated position to grasp tissue between the first and second jaw members, and further moved from the approximated position to the second position to provide an over-compressive force to the jaw members, the first jaw member over-travels past the longitudinal axis and the second jaw member deflects relative to the longitudinal axis against a bias of the living hinge exposing the knife from the channel to cut tissue disposed between the first and second jaw members.

10. The surgical instrument according to claim 9, wherein, in the approximated position, the jaw members are configured to grasp tissue with a clamping pressure in the range of about 3 kg/cm$^2$ to about 16 kg/cm$^2$.

11. The surgical instrument according to claim 10, wherein when the clamping pressure between jaw members exceeds 16 kg/cm$^2$, the second jaw member deflects relative to the longitudinal axis to expose the knife.

12. The surgical instrument according to claim 9, wherein the first jaw member includes a channel defined therein in vertical registration with the channel defined within the second jaw member, the channel defined in the first jaw member configured to receive the knife as the first jaw member over-travels past the longitudinal axis and the second jaw member deflects about the living hinge.

13. The surgical instrument according to claim 9, wherein the over-travel of the first jaw member against the second jaw member causes the second jaw member to deflect in a tip-biased manner thereby initially exposing a distal end of the knife and cutting tissue in a distal-to-proximal manner as the knife is further exposed.

14. A method for treating and cutting tissue, comprising:
   actuating a handle of a surgical instrument to grasp tissue between a first and second jaw member of an end effector assembly under a first pressure;
   applying electrosurgical energy to the jaw members to treat the tissue grasped therebetween;
   further actuating the handle to cause the first jaw member to over-travel past a longitudinal axis defined through the second jaw member thereby causing the second jaw member to deflect about a living hinge relative to the longitudinal axis and expose a knife for severing tissue grasped between the jaw members.

\* \* \* \* \*